United States Patent
Reindler

(10) Patent No.: US 6,512,011 B1
(45) Date of Patent: Jan. 28, 2003

(54) BUPROPION TO TREAT HERPES VIRAL DISEASES

(75) Inventor: Christopher William Reindler, Como (AU)

(73) Assignee: CC Capital Partners Inc., Toronto (CA)

(*) Notice: Subject to any disclaimer, the term of this patent is extended or adjusted under 35 U.S.C. 154(b) by 0 days.

(21) Appl. No.: 09/787,024

(22) PCT Filed: Dec. 7, 1999

(86) PCT No.: PCT/AU99/01089

§ 371 (c)(1),
(2), (4) Date: Jan. 11, 2002

(87) PCT Pub. No.: WO00/38827

PCT Pub. Date: Jun. 15, 2000

Related U.S. Application Data

(60) Provisional application No. 60/135,494, filed on Dec. 8, 1998.

(51) Int. Cl.[7] ............................................. A61K 31/137
(52) U.S. Cl. ..................................................... 514/649
(58) Field of Search .......................................... 514/649

(56) References Cited

U.S. PATENT DOCUMENTS

| | | | | |
|---|---|---|---|---|
| 4,438,138 A | * | 3/1984 | Stern | 424/330 |
| 4,507,323 A | * | 3/1985 | Stern | 514/649 |
| 5,753,712 A | * | 5/1998 | Pinsker | 514/649 |

FOREIGN PATENT DOCUMENTS

| | | | |
|---|---|---|---|
| WO | 97/29735 | * | 8/1997 |

OTHER PUBLICATIONS

Fernandez F., et al., "Psychopharmacotherapy of Psychiatric Syndromes in Asymptomatic and Symptomatic HIV Infection", *Psychiatric Medicine*, vol. 9, No. 3, pp 337–394, 1991.

Fichtner C.G., et al, "Bupropion–Associated Mania In a Patient with HIV Infection", *Journal of Clinical Psychopharmacology*, vol. 2, No. 5, pp 366–367, 1992.

Avants, S.K., et al., A Comprehensive Pharmacologic–Psychosocial Treatment Program for HIV–Seropositive Cocaine–and Opioid–Dependent Patients, *Journal of Substance Abuse Treatment*, vol. 15, No. 3pp. 261–265, 1998.

* cited by examiner

Primary Examiner—Phyllis G. Spivack
(74) Attorney, Agent, or Firm—Kenyon & Kenyon

(57) ABSTRACT

Methods are disclosed for the treatment of a herpes viral infection in a human or animal subject by administering bupropion or a physiologically acceptable salt, solvate or enantiomer thereof. Most particularly, the virus is HSV1 or HSV2.

16 Claims, No Drawings

BUPROPION TO TREAT HERPES VIRAL DISEASES

This application claims the benefit of Provisional application No. 60/135,494, filed Dec. 8, 1998 now abandoned.

FIELD OF THE INVENTION

This invention relates to a new medical use for bupropion and physiologically acceptable salts and solvates thereof. Specifically the invention concerns the use of bupropion in treating viral infections, more particularly infections caused by viruses of the Herpes family.

BACKGROUND OF THE INVENTION

Bupropion hydrochloride, (±)-1-(3-chlorophenyl)-2-[(1,1-di-methylethyl)-amino]-1-propanone hydrochloride has been used for the treatment of depression. Bupropion is a relatively weak inhibitor of the neuronal uptake of noradrenaline (NA), serotonin and dopamine (DA), and does not inhibit monoamine oxidase. While the mechanism of action of bupropion, as with other antidepressants, is unknown, it is presumed that this action is mediated by noradrenergic and/or dopaminergic mechanisms. Available evidence suggests that bupropion is a selective inhibitor of noradrenaline (NA) at doses that are predictive of antidepressant activity in animal models. See Ascher, J. A., et al., Bupropion: A Review of its Mechanism of Antidepressant Activity. *Journal of Clinical Psychiatry*, 56: p. 395–401,1995.

It has also been disclosed that bupropion is useful for the treatment of migraine (U.S. Pat. No. 5,753,712), reducing cholesterol (U.S. Pat. No. 4,438,138), treatment of minimal brain dysfunction (U.S. Pat. No. 4,435,449), treatment of tardive dyskinesia (U.S. Pat. No. 4,425,363), reversing impaired mental alertness due to ethanol consumption (U.S. Pat. No. 4,393,078), treatment of psychosexual dysfunction (U.S. Pat. No. 4,507,323), suppressing prolactin secretion (U.S. Pat. No. 4,347,257) and as an aid to smoking cessation.

The Herpes family of viruses is responsible for a wide range of infectious diseases in several species, including chicken pox, shingles, retinitis, pneumonitis and keratitis in humans and diseases of the skin and mucosa, including keratitis in rabbits, herpetic encephalitis in mice, Herpes viruses include *Herpes zoster*, HSV1 and HSV2 (Herpes Simplex Virus type 1 and type 2), hCMV and mCMV (human and murine cytomegalovirus), VZV (varicella zoster virus), EBV (Epstein barr virus) HHV6 and HHV8 (human herpes viruses, types 6 and 8).

There is a need in the art to develop novel therapies for the treatment and prevention of viral infections such as infections caused by the Herpes virus.

SUMMARY OF THE INVENTION

The present inventor has surprisingly demonstrated that bupropion is useful for the prevention and treatment of viral infections. In particular, the inventor has shown that bupropion is useful for the treatment and prevention of certain symptoms of viral infections caused by a herpes virus. More specifically, the inventor has shown bupropion is useful for the treatment of symptoms caused by a Herpes Simplex Virus. Bupropion is thus of potential benefit in the treatment of infections of viruses of the Herpes family or conditions caused thereby, particularly Herpes Simplex Virus (HSV) 1, HSV2, *Herpes zoster* and *Varicella zoster*.

Accordingly, the present invention provides a use of bupropion for the manufacture of a medicament for the prevention or treatment of a viral infection. The present invention also provides a use of bupropion to prevent or treat a viral infection. The present invention further provides a method of treating and preventing a viral infection comprising administering an effective amount of bupropion to an animal in need thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

As hereinbefore mentioned, the present inventor has demonstrated that bupropion is useful in the prevention or treatment of viral infections. The present inventor has shown that bupropion is superior to many other anti-viral agents such as acyclovir and famciclovir in the treatment and prevention of infections caused by the herpes virus.

Accordingly, the present invention provides a use of bupropion or a physiologically acceptable salt, solvate or enantiomer thereof for the manufacture of a medicament for the prevention or treatment of a viral infection. The present invention also provides a use of bupropion or a physiologically acceptable salt, solvate or enantiomer thereof to prevent or treat a viral infection. The present invention further provides a method of treating and preventing a viral infection comprising administering an effective amount of bupropion or a physiologically acceptable salt, solvate or enantiomer thereof to an animal in need thereof.

The term "effective amount" as used herein is an amount effective, at dosages and for periods of time necessary to treat or prevent a viral infection.

The term "animal" as used herein includes all members of the animal kingdom including humans.

The term "bupropion" as used herein includes all physiologically acceptable salts and solvates thereof and all enantiomers thereof.

The bupropion for use in the invention is suitably in the form of a physiologically acceptable salt. This salt may include an acid addition salt formed with organic or inorganic acids for example hydrochloride, hydrobromide, sulphate, nitrate, phosphate, formate, mesylate, citrate, benzoate, fumarate, maleate and succinate. Preferably, the bupropion is in the form of its hydrochloride salt. The chemical structure of bupropion hydrochloride is shown below.

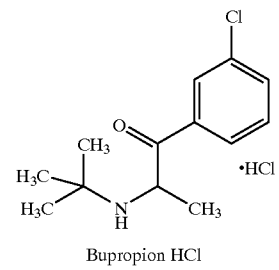

Bupropion HCl

Bupropion for use according to the invention may be administered as the raw chemical comprising the active compound. Preferably, the bupropion is formulated into a pharmaceutically acceptable composition or medicament. Conveniently, bupropion for use according to the invention may be formulated in conventional manner using one or more pharmaceutically acceptable excipients. Thus, bupropion for use according to the invention may for example be formulated for oral, sub-lingual, buccal, parenteral, rectal or intranasal administration or in a form suitable for administration by inhalation or insufflation (either through the mouth or nose).

For oral administration the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl P-hydroxybenzoates or sorbic acid).

For buccal administration, the compositions may take the form of tablets or lozenges formulated in conventional manner.

Bupropion for use according to the invention may be formulated for parenteral administration by injection, conveniently intravenous, in intramuscular or subcutaneous injection. Formulations for injection may be presented in unit dosage form e.g. in ampoules or in multi-dose containers, optionally with an added preservative.

The compositions for parenteral administration may take such forms as suspensions, solutions or emulsions in oily or aqueous vehicles, and may contain formulatory agents such as suspending, stabilising and/or dispersing agents. Alternatively, the active ingredient may be in dry form such as a powder, crystalline or freeze-dried solid for constitution with a suitable vehicle, e.g. sterile pyrogen-free water or isotonic saline before use. They may be presented, for example, in sterile ampoules or vials.

Bupropion for use according to the invention may also be formulated in rectal compositions such as suppositories or retention enemas, e.g. containing conventional suppository bases such as cocoa butter or other glyceride. Tablets for sub-lingual administration may be formulated in a conventional manner.

For intranasal administration, bupropion for use according to the invention may be used, for example, as a liquid in the form of a spray or drops or as a powder. Suitably the preparation for intranasal administration is delivered in the form of a spray or aerosol from an insufflator or from a pressurised pack or nebuliser with the use of a suitable propellant.

For administration by inhalation, bupropion for use according to the invention is conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of gelatin for use in an inhaler or insufflater may be formulated containing a powder mix of a compound of use in the invention and a suitable powder base such as lactose or starch.

Various formulations of bupropion have been disclosed in U.S. Pat. Nos. 5,427,798, 5,358,970, 5,541,231, 5,731,000 and 5,763,493 (and other patents related to U.S. Pat. No. 5,358,970) all of which are incorporated herein by reference.

As indicated above, bupropion is of therapeutic and prophylactic benefit in the treatment of viral infections. In particular, bupropion is useful in the prevention and treatment of infectious diseases and conditions caused by viral infections. Such diseases include chicken pox (*Varicella zoster*), shingles (*Herpes zoster*), keratitis in rabbits, herpetic encephalitis in mice, cutaneous herpes in guinea pigs, cold sores (herpes labialis) and genital herpes (herpes simplex virus) in humans, retinitis, pneumonitis and keratitis in humans (hCMV), as well as diseases caused by Epstein Barr Virus (EBV), human herpes virus 6 (HHV 6), HHV 7 and HHV 8 and Human Immune deficiency Virus (HIV). Of particular mention are chicken pox, shingles, cold sores and genital herpes in humans; of special mention are cold sores and genital herpes in humans.

The terms "treatment and prevention" include the prophylaxis, prevention of recurrence of symptoms and suppression or amelioration of symptoms (whether mild, moderate or severe) as well as the treatment of established conditions caused by a viral infection.

It will be appreciated that the precise dose of bupropion administered will in general depend on the age and condition of the patient and the frequency and route of administration and will be at the ultimate discretion of the attendant physician. The compound may be administered in single or divided doses and may be administered one or more times, for example 1 to 4 times per day, for one or two days.

Typically, bupropion is useful for the treatment and prevention of a viral infection in an amount between 0.1 mg to 1000 mg per day, more preferably in an amount between 25 mg and 600 mg per day and most preferably in an amount between 150 mg to 300 mg per day. Preferably, the bupropion is given for at least two days.

Typically, pharmaceutical compositions comprise bupropion in the amount of 0.1 mg to 500 mg per unit dose, more preferably in an amount between 25 mg and 300 mg per unit dose and most preferably in an amount between 50 mg to 150 mg per unit dose.

The total amount of bupropion taken to prevent or treat a viral infection or a particular episode of a recurrent viral infection is typically between about 50 mg and about 2000 mg, more preferably between about 150 mg and about 1500 mg, most preferably between about 300 mg and 1200 mg.

The bupropion may be administered in combination with other anti-viral agents that are useful in the treatment or prevention of a viral infection, such as infections caused by a herpes virus.

The following non-limiting examples are illustrative of the present invention:

EXAMPLES

The following examples illustrate that demonstrate that bupropion is effective in preventing and treating herpes virus infections.

Example 1

The first case treated was CR a 50 year old businessman with recurrent genital Herpes Simplex viral infection. There were 5–6 recurrences per year. Acyclovir was partially effective in aborting the attacks as the severity of the attacks was reduced slightly the duration of the attacks was reduced from 2 weeks to 5–7 days. The subject took bupropion which resulted in an alteration of the course of the attack and within 2 days, the attack was aborted. Since that time, whenever the subject feels that an attack is about to commence, 4 doses of bupropion, each dose containing 150 mg of bupropion, are taken over 2 days and this either aborts the attack completely, or reduces it to a small crop of lesions which heal completely within 48 hours. There has not been a single significant recurrence of the sort that existed, since commencing this regime over one year ago.

Example 2

The second case was a 36-year-old nurse, DB. She developed HSV I involving the right upper lip and nares (cold sores). She has approximately 1 episode per month related to menstrual periods. This has been occurring for the last 6 years and has lasted for at least a week of every month. The severity varied according to her general state of health and stress levels. The outbreaks lasted at least one week and have made a significant impact on her psychological state. She has not been on systemic therapy. Topical therapy does not change the duration of the lesions, but prevents the secondary infections that she is prone to without topical therapy.

The commencement of bupropion, 300 mg twice daily, for 2 days on day 2 of an outbreak resulted in complete resolution of her lesions by the end of day 3. A minor recurrence of the lesions one week later was aborted by a similar dosage within the first day.

Example 3

The third case was GH, a 28-year-old entrepreneur. He has a coffee shop chain. He is thus very visible and he is very self-conscious of even minor blemishes on his face. He has mild herpes labialis (cold sores), which occurs approximately 5 times a year. He has taken intermittent acyclovir and has even considered continuous acyclovir, because of his image. He is also aware when an attack is going to occur and taking acyclovir with the tingling has reduced his attacks to barely detectable and lasting 3 days. After taking 2 tablets of bupropion (each containing 150 mg) when he feels the tingling, he has not had an eruption in the last 3 months.

Example 4

The fourth case was JR, a 22-year-old student with extensive genital herpes. He has had 4 attacks thus far, which have been treated initially with acyclovir and then later with famciclovir. The normal duration of these attacks on these agents was 5–7 days. He was unable to attend classes and took a further 2 weeks before he felt normal. A big feature of his illness is the severe fatigue that precedes and follows his attacks. The subject took bupropion, 300 mg twice daily, for 2 days and he was feeling well. The lesions had cleared completely and they had not been as bad as usual. He had not developed any post-viraemia fatigue either. He later used a further 2 day course when he felt tingling. He did not develop any eruptions at that time.

Example 5

The fifth case was SC, a 45-year-old medical secretary with recurrent herpes labialis. He had been paying for acyclovir privately, despite the cost, because of his wish to suppress his frequent and unsightly lesions. He had however, been getting breakthrough lesions on the acyclovir and he was concerned that his herpes had become resistant to this agent. He took bupropion in combination with acyclovir with good results. An attack was treated within 24 hours on the two agents. Since then, he has had two further episodes where he felt tingling of the lip. He took bupropion, 150 mg every 12 hours for 2 days. No outbreak of herpes labialis occurred with either of these episodes.

Example 6

The sixth case was AB, a 49-year-old reporter. He developed hypertension and mild renal impairment on acyclovir. This was given for recurrent buttock herpes simplex II. This was ceased and after 1 year, the hypertension and renal impairment reverted to normal. Famciclovir successfully suppressed his disease, but he still had minor outbreaks on continuous therapy approximately once every 2–3 months. He started taking bupropion with onset of his pre-outbreak symptoms and he has reported that he has not had an eruption since.

Example 7

The seventh case was AW a 26-year-old woman who from infancy has developed severe herpes labialis (cold sores) every 2 months. This involved the nares, upper and lower lips bilaterally. Even after topical acyclovir, the course of the illness was 2 weeks of significant outbreak. She took bupropion and within 36 hours of taking 300 mg, she did not progress from her initial lesion on the left upper lip. She developed a rash—which prove to be scarlet fever. Her partner also developed scarlet fever as well. The lesion started disappearing after 3 days and by day 5 was hardly noticeable. The scarlet fever did not worsen on the bupropion. It should be noted that this patient is usually very intolerant of medications and tends to vomit easily. No side effects were noticed on bupropion.

Example 8

The eighth case that was treated with bupropion was a medical receptionist. Her normal herpes labialis lasted between 5 and 7 days. Topical therapy with acyclovir has been unhelpful in the past. She developed a lesion on the right side of her chin and was given bupropion 150 mg twice daily for 2 days. Within 24 hours, the lesion had dried out and was scabbing within the next 12 hours. There was complete resolution 3 days later.

The physician conducting the above trials has reported that the results thus far have been beyond expectation. He is commented that "not only has there been a success from a completely unlikely agent, but there has also been a success beyond that achieved by the well-established anti-viral agents".

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

I claim:

1. A method of treating or preventing a recurrence of a herpes viral infection comprising administering an effective amount of bupropion or a physiologically acceptable salt, solvate or enantiomer of bupropion to an animal in need thereof.

2. A method according to claim 1 wherein the herpes viral infection is caused by a virus selected from the group consisting of Herpes zoster, Herpes Simplex Virus type 1, Herpes Simplex Virus type 2, and Herpes labialis.

3. A method according to claim 1 wherein the herpes virus is a herpes simplex virus.

4. A method according to claim 3 wherein the herpes simplex virus is Herpes Simplex Virus type 1, HSV1.

5. A method according to claim 1 wherein the herpes virus is Herpes labialis.

6. A method according to claim 1 wherein the bupropion is administered in an amount from about 0.1 mg to about 500 mg per unit dose.

7. A method according to claim 6 wherein the bupropion is administered in an amount from about 25 mg to about 300 mg per unit does.

8. A method according to claim 6 wherein the bupropion is administered in an amount from about 50 mg to about 150 mg per unit dose.

9. A method according to claim 6 wherein the effective amount of bupropion is from about 50 to 2000 mg.

10. A method according to claim 9 wherein the effective amount of bupropion is administered in at least two doses.

11. A method according to claim 9 wherein the effective amount of bupropion is administered in at least four doses.

12. A method according to claim 6 wherein the effective amount of bupropion is from about 300 to 1200 mg.

13. A method according to claim 1 wherein the animal is a human.

14. The method according to claim 1 wherein the effective amount of bupropion is formulated as an oral dosage form.

15. The method according to claim 1 wherein the bupropion is administered in combination with another antiviral agent.

16. The method according to claim 15 wherein the antiviral agent is acyclovir.

* * * * *

UNITED STATES PATENT AND TRADEMARK OFFICE
CERTIFICATE OF CORRECTION

PATENT NO.    : 6,512,011 B1                                                Page 1 of 1
DATED         : January 28, 2003
INVENTOR(S)   : Christopher Reindler It is certified that error appears in the above-identified patent and that said Letters Patent is hereby corrected as shown below:

<u>Title page,</u>
Item [73], "CC Capital Partners Inc., Toronto (CA)" should be
-- Planisphere Corp., Bridgetown (BB) --

Signed and Sealed this

Twenty-seventh Day of May, 2003

JAMES E. ROGAN
*Director of the United States Patent and Trademark Office*